US009605297B2

(12) United States Patent
Zhuang et al.

(10) Patent No.: US 9,605,297 B2
(45) Date of Patent: Mar. 28, 2017

(54) METHOD OF GENERATING LINKAGE-SPECIFIC DI-AND POLYPROTEIN PROBES

(71) Applicants: Zhihao Zhuang, Wilmington, DE (US); Guorui Li, Baltimore, MD (US)

(72) Inventors: Zhihao Zhuang, Wilmington, DE (US); Guorui Li, Baltimore, MD (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 15/029,519

(22) PCT Filed: Oct. 15, 2014

(86) PCT No.: PCT/US2014/060638
§ 371 (c)(1),
(2) Date: Apr. 14, 2016

(87) PCT Pub. No.: WO2015/057803
PCT Pub. Date: Apr. 23, 2015

(65) Prior Publication Data
US 2016/0237471 A1  Aug. 18, 2016

Related U.S. Application Data

(60) Provisional application No. 61/891,571, filed on Oct. 16, 2013.

(51) Int. Cl.
| | |
|---|---|
| C07D 317/28 | (2006.01) |
| C12Q 1/37 | (2006.01) |
| C07K 14/47 | (2006.01) |
| C07K 1/10 | (2006.01) |

(52) U.S. Cl.
CPC ............. *C12Q 1/37* (2013.01); *C07D 317/28* (2013.01); *C07K 1/10* (2013.01); *C07K 14/47* (2013.01); *C07K 2319/50* (2013.01); *C07K 2319/95* (2013.01); *G01N 2333/95* (2013.01); *G01N 2440/36* (2013.01)

(58) Field of Classification Search
None
See application file for complete search history.

(56) References Cited

U.S. PATENT DOCUMENTS

| | | | | |
|---|---|---|---|---|
| 3,992,408 | A * | 11/1976 | Gall | ..................... C07D 209/48 548/465 |
| 4,139,540 | A | 2/1979 | Heeres | |
| 4,485,099 | A | 11/1984 | Boger | |
| 2012/0107857 | A1 | 5/2012 | Chelur | |
| 2013/0102012 | A1 | 4/2013 | Komander | |
| 2014/0072992 | A1 | 3/2014 | Chelur | |

(Continued)

OTHER PUBLICATIONS

Zaragosa, Ivann et al, "A synthetic approach to the actinophyllic acid molecular architecture." Tet. Lett. (2013) 54 p. 2180-2182.*
Veale et al., "The synthesis, N-alkylation and epimerisation study of a phthaloyl derived thiazolidine", Tetrahedron 64, 2008, pp. 6794-6800.
Amerik, et al., "Mechanism and function of deubiquitinating enzymes", Biochimica et Biophysica 1694 (2004), pp. 189-207.
Sadaghiani, et al., "Tagging and detection strategies for activity-based proteomics", Current Opinion in Chemical Biology, vol. 11, 2007, pp. 20-28.
Borodovsky et al., "A novel active site-directed specific for deubiquitylating enzymes reveals proteasome association of USP14", The Embo Journal, vol. 20, No. 18, 2001, pp. 5187-5196.
Altun et al., "Activity-Based Chemical Proteomics Accelerates Inhibitor Development for Deubiquitylating Enzymes", Chemisty & Biology vol. 18, Nov. 23, 2011, pp. 1401-1412.
Avvakumov et al., "Amino-terminal Dimerization, NRDP1-Rhodanese Interaction, and Inhiited Catalytic Domain Confirmation of the Ubiquitin-specific Protease 8 (USP8)", Journal of Biological Chemistry, vol. 281, No. 49, Dec. 8, 2006, pp. 38061-38070.
Sato et al., "Structural basis for specific cleavage of Lys 63-linked polyubiquitin chains", Nature, vol. 455, Sep. 18, 2008, pp. 358-364.
Cravatt et al., "Activity-Based Protein Profiling: From Enzyme Chemistry to Proteomic Chemistry", Annu. Rev. Biochem, vol. 77, 2008, pp. 383-414.
Bavikar et al., "Chemical Synthesis of Ubiquitinated Peptides with Varying Lengths and Types of Ubiquitin Chains to Explore the Activity of Deubiquitinases", Angew. Chem. Int. Ed., vol. 51, 2012, pp. 758-763.
Bozza et al., "Transient Kinetic Analysis of USP2-Catalyzed Deubiquitination Reveals a Conformational Rearrangement in the K48-Linked Diubiquitin Substrate", Biochemisty, vol. 51, 2012, pp. 10075-10086.
McGouran et al., "Fluorescence-based active site probes for profiling deugiquitinating enzymes", Org. Biomol. Chem, vol. 10, 2012, pp. 3379-3383.
Little et al., "A Simple and Practical Synthesis of 2-Aminoimidazoles", J. Org. Chem, vol. 59, 1994, pp. 7299-7305.
Faesen et al., "Mechanism of USP7/HAUSP Activation by its C-Terminal Ubiquitin-like Domain and Allosteric Regulation by GMP-Synthetase", Molecular Cell, vol. 44, Oct. 7, 2011, pp. 147-159.
Huib Ovaa, "Active-Site directed probes to report enzymatic action in the ubiquitin proteasome system", Nature Reviews, vol. 7, Aug. 2007, pp. 613-620.
Ekkebus et al., "On Terminal Alkynes That Can React with Active-Site Cysteiine Nucleophiles in Proteases", J. Am. Chem. Soc. vol. 135, 2013, pp. 2867-2870.

(Continued)

*Primary Examiner* — Fred Reynolds
(74) *Attorney, Agent, or Firm* — RatnerPrestia

(57) ABSTRACT

Deubiquitinating enzyme (DUB) probes are provided that resemble native diubiquitin (diUB) with a similar linkage size and that may contain a Michael acceptor for trapping the DUB active-site cysteine. For example, both K63- and K48-linked diubiquitin probes are generated using a facile chemical ligation method, utilizing the linker compound 3-(2-(bromomethyl)-1,3-dioxolan-2-yl)prop-2-en-1-amine. The diUb probes are capable of labelling DUBs from different families and may be employed to reveal intrinsic linkage specificities of DUBs.

18 Claims, 3 Drawing Sheets

(56) References Cited

OTHER PUBLICATIONS

Keusekotten et al., "OTULIN Antagonizes Lubac Signaling by Specifically Hydrolyzing Met1-Lined Polyubiquitin", Cell, vol. 153, Jun. 6, 2013, pp. 1312-1326.
Iphofer et al., "Profiling Ubiquitin Linkage Specificities of Deubiquitinating Enzymes with Branched Ubiquitin Isopeptide Probes", ChemBioChem, vol. 13, 2012, pp. 1416-1420.
Chen, et al., "Selective and Cell-Active Inhibitors of the USP1/UAF1 Deubiquitinase Complex Reverse Cisplatin Resistance in Non-small Cell Lung Cancer Cells", Chemistry & Biology, vol. 18, Nov. 23, 2011, pp. 1390-1400.
Renatus et al., "Structural Basis of Ubiquitin Recognition by the Deubiquitinating Protease USP2", Structure, vol. 14, Aug. 2006, pp. 1293-1302.
Love et al., "Ubiquitin C-Terminal Electrophiles Are Activity-Based Probes for Identification and Mechanistic Study of Ubiquitin Conjugating Machinery", ACS Chemical Biology, vol. 4, No. 4, Oct. 17, 2008, pp. 275-287.
Borodovsky et al., "Chemistry-Based Functional Proteomics Reveals Novel Members of the Deubiquitinating Enzyme Family", Chemisty & Biology, vol. 9, Oct. 2002, pp. 1149-1159.
de Jong et al., "Ubiquitin-Based Probes Prepared by Totl Synthesis to Profile the Acitvity of Deubiquitinating Enzymes", ChemBioChem, vol. 13, 2012, pp. 2251-2258.
Reyes-Turcu et al., "Regulation and Cellular Roles of Ubiquitin-Specific Deubiquitinating Enzymes", Annu. Rev. Biochem., vol. 78, 2009, pp. 363-397.
Kimple et al., "Affinity Tag for Protein Purification and Detection Based on the Disulfide-Linked Complex of InaD and NorpA", BioTechniques, vol. 33, No. 3, 2002, pp. 578-590.
Shanmugham et al., "Nonhydrolyzable Ubiquitin—Isopeptide Isosteres as Deubiquitinating Enzyme Probes", J. Am. Chem. Soc., vol. 132, pp. 8834-8835.
International Search Report and Written Opinion of the International Searching Authority issued in related International Application No. PCT/US2014/060638, dated Jan. 26, 2015.
International Preliminary Report on Patentability issued in related International Application No. PCT/US2014/060638, dated Apr. 19, 2016.

* cited by examiner

METHOD OF GENERATING LINKAGE-SPECIFIC DI-AND POLYPROTEIN PROBES

CROSS-REFERENCE TO RELATED APPLICATIONS

This application is a national phase of International Application No. PCT/US2014/060638, filed Oct. 15, 2014, which claims priority from U.S. Provisional Application No. 61/891,571, filed Oct. 16, 2013, the entire disclosure of each of which is incorporated herein by reference for all purposes.

STATEMENT REGARDING FEDERALLY SPONSORED RESEARCH

This invention was made with government support under grant or contract number R01GM097468, awarded by the National Institutes of Health. The United States government has certain rights in this invention.

FIELD OF THE INVENTION

The present invention pertains to deubiquitinating enzyme (DUB) probes that resemble native diubiquitin (diUB) with a similar linkage size and that may contain a Michael acceptor for trapping the DUB active-site cysteine, as well as methods for making such probes.

DISCUSSION OF THE RELATED ART

Deubiquitinating enzymes (DUBs) are essential for many cellular pathways and have emerged as promising targets for pharmacological intervention. See F. E. Reyes-Turcu, K. H. Ventii and K. D. Wilkinson, *Annu Rev Biochem*, 2009, 78, 363-397; and A. Y. Amerik and M. Hochstrasser, *Biochimica et biophysica acta*, 2004, 1695, 189-207. DUBs exert effects by reversing the mono- and polyubiquitination of a large number of proteins in various cellular pathways. Activity-based probes (ABPs) have been widely used in profiling different classes of enzymes. See B. F. Cravatt, A. T. Wright and J. W. Kozarich, *Annu Rev Biochem*, 2008, 77, 383-414; and A. M. Sadaghiani, S. H. Verhelst and M. Bogyo, *Current opinion in chemical biology*, 2007, 11, 20-28. In recent years, ABPs have also been developed for DUBs. See H. Ovaa, *Nature reviews. Cancer*, 2007, 7, 613-620. The most widely used DUB probe is a monoubiquitin with an electrophilic group introduced at its C-terminus, such as ubiquitin-vinylsulfone (Ub-VS) or ubiquitin-vinylmethyl ester (Ub-VME). See A. Borodovsky, B. M. Kessler, R. Casagrande, H. S. Overkleeft, K. D. Wilkinson and H. L. Ploegh, *Embo J*, 2001, 20, 5187-5196; and A. Borodovsky, H. Ovaa, N. Kolli, T. Gan-Erdene, K. D. Wilkinson, H. L. Ploegh and B. M. Kessler, *Chemistry & biology*, 2002, 9, 1149-1159. This approach has been further extended by either varying the C-terminal electrophilic group, aiming to improve reactivity or introducing a fluorescent group for easy readout. See R. Ekkebus, S. I. van Kasteren, Y. Kulathu, A. Scholten, I. Berlin, P. P. Geurink, A. de Jong, S. Goerdayal, J. Neefjes, A. J. R. Heck, D. Komander and H. Ovaa, *Journal of the American Chemical Society*, 2013, 135, 2867-2870; K. R. Love, R. K. Pandya, E. Spooner and H. L. Ploegh, *Acs Chem Biol*, 2009, 4, 275-287; J. F. McGouran, H. B. Kramer, M. M. Mackeen, K. di Gleria, M. Altun and B. M. Kessler, *Organic & Biomolecular Chemistry*, 2012, 10, 3379; and A. de Jong, R. Merkx, I. Berlin, B. Rodenko, R. H. Wijdeven, D. El Atmioui, Z. Yalcin, C. N. Robson, J. J. Neefjes and H. Ovaa, *ChemBioChem*, 2012, 13, 2251-2258.

Although the monoubiquitin DUB probes have proven to be useful tools for profiling DUBs, they provide no information of the chain linkage- and target-specificity of DUBs because the probes contain no ubiquitin acceptor protein. Recent publications have described DUB probes in which a peptide derived from the proximal ubiquitin was conjugated to the C-terminus of an intact ubiquitin. See A. Shanmugham, A. Fish, M. P. A. Luna-Vargas, A. C. Faesen, F. E. Oualid, T. K. Sixma and H. Ovaa, *Journal of the American Chemical Society*, 2010, 132, 8834-8835; A. Iphöfer, A. Kummer, M. Nimtz, A. Ritter, T. Arnold, R. Frank, J. van den Heuvel, B. M. Kessler, L. Jänsch and R. Franke, *ChemBioChem*, 2012, 13, 1416-1420; and S. N. Bavikar, L. Spasser, M. Haj-Yahya, S. V. Karthikeyan, T. Moyal, K. S. Kumar and A. Brik, *Angew Chem Int Ed Engl*, 2012, 51, 758-763. However, high resolution structures of DUBs in complex with diubiquitin showed that in addition to the peptide flanking the ubiquitinated lysine residue, more extensive interactions between DUB and the proximal ubiquitin also contribute to the diubiquitin recognition by DUB. See K. Keusekotten, P. R. Elliott, L. Glockner, B. K. Fiil, R. B. Damgaard, Y. Kulathu, T. Wauer, M. K. Hospenthal, M. Gyrd-Hansen, D. Krappmann, K. Hofmann and D. Komander, *Cell*, 2013, 153, 1312-1326; and Y. Sato, A. Yoshikawa, A. Yamagata, H. Mimura, M. Yamashita, K. Ookata, O. Nureki, K. Iwai, M. Komada and S. Fukai, *Nature*, 2008, 455, 358-362. In particular, residues in the proximal ubiquitin that are distant from the modified lysine residue were found to contribute to the diubiquitin binding and DUB catalysis. Therefore, it would be desirable to develop diubiquitin probes that harbor an intact proximal ubiquitin in order to probe the ubiquitin chain-linkage specificity of DUBs.

BRIEF SUMMARY OF THE INVENTION

One aspect of the invention provides compounds having a structure in accordance with Formula (I):

$$H_2NCH_2—R—C(Diox)CH_2X \qquad (I)$$

wherein R is —$CH_2CH_2$— or —CH=CH—, Diox is —$O(CH_2)_nO$— with n=2 or 3 and forms a 1,3-dioxolane ring or 1,3-dioxane ring which includes the carbon atom to which the oxygen atoms of —$O(CH_2)_nO$— are both bonded, and X is Br, Cl or I, which are useful as linker compounds in the preparation of di- and polyproteins. Specific illustrative examples of such compounds include 3-(2-(bromomethyl)-1,3-dioxolan-2-yl)prop-2-en-1-amine (R=—CH=CH—, n=2, X=Br) and 3-(2-(bromomethyl)-1,3-dioxolan-2-yl)propan-1-amine (R=—$CH_2CH_2$—, n=2, X=Br).

Such linker compounds may be synthesized using the methods described in more detail hereafter. However, generally speaking, the linker compounds may be obtained by hydrolysis, particularly base-catalyzed hydrolysis, of a precursor compound having a structure in accordance with Formula (II):

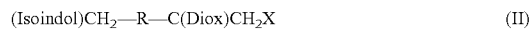

$$(Isoindol)CH_2—R—C(Diox)CH_2X \qquad (II)$$

wherein Isoindol is an isoindoline-1,3-dione moiety, R is —$CH_2CH_2$— or —CH=CH—, and Diox is —$O(CH_2)_nO$— with n=2 or 3 and forms a 1,3-dioxolane ring or 1,3-dioxane ring which includes the carbon atom to which the oxygen atoms of —$O(CH_2)_nO$— are both bonded, and X is Br, Cl or I.

The hydrolysis is carried out under conditions such that the isoindoline-1,3-dione ring is selectively hydrolyzed while preserving the 1,3-dioxolane ring or 1,3-dioxane ring.

The precursor compound may be prepared by converting the carbonyl group adjacent to the halomethyl group —CH$_2$X in a compound having a structure in accordance with Formula (III) to a 1,3-dioxolane ring or a 1,3-dioxane ring by reaction with ethylene glycol or 1,3-propanediol, respectively, under acid-catalyzed conditions:

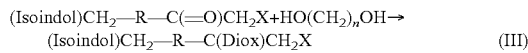

(Isoindol)CH$_2$—R—C(Diox)CH$_2$X    (III)

n=2 or 3

For example, the linker compound 3-(2-(bromomethyl)-1,3-dioxolan-2-yl)prop-2-en-1-amine may be prepared using a method comprising hydrolyzing 2-(3-(2-(bromomethyl)-1,3-dioxolan-2-yl)allyl)isoindoline-1,3-dione. The 2-(3-(2-(bromomethyl)-1,3-dioxolan-2-yl)allyl)isoindoline-1,3-dione may be prepared by reacting 2-(3-(2-(bromomethyl)-1,3-dioxolan-2-yl)allyl)isoindoline-1,3-dione and ethylene glycol.

Also provided by the present invention is a di- or polyprotein comprising a first polypeptide moiety covalently bonded to a second polypeptide moiety through a linkage having a structure corresponding to —[C(=O)NHCH$_2$C(=O)NHCH$_2$—R—C(=O)CH$_2$SCH$_2$]—, wherein R is —CH$_2$CH$_2$— or —CH=CH—. For example, the first polypeptide moiety may be a first ubiquitin moiety and the second polypeptide moiety may be a second ubiquitin moiety, thereby providing a di- or polyubiquitin. The linkage may link a C-terminus of the first ubiquitin moiety with position 6, 11, 27, 29, 33, 48 or 63 of the second ubiquitin moiety. In another aspect of the invention, the linkage links position 75 of the first ubiquitin moiety with position 6, 11, 27, 29, 33, 48 or 63 of the second ubiquitin moiety. The first ubiquitin moiety may be a Ub$_{1-75}$ moiety, for example. The first and/or second polypeptide moiety may bear a reporter tag. For example, the second ubiquitin moiety may bear a reporter tag. In various aspects of the invention, the reporter tag may, for example, be selected from the group consisting of affinity tags, biotin and fluorophores. Illustrative examples of suitable reporter tags include affinity tags selected from the group consisting of HA-tag, His-tag, FLAG-tag, and Myc-tag.

In a further aspect of the invention, the first polypeptide moiety is a first ubiquitin moiety and the second polypeptide moiety is a moiety other than a ubiquitin moiety. The second polypeptide moiety may, for example, be a moiety selected from the group consisting of PCNA moieties, histone moieties and α-synuclein moieties. The linkage may link a C-terminus of the first ubiquitin moiety with a cysteine residue of the second polypeptide moiety. In another embodiment, the linkage links position 75 of the first ubiquitin moiety with a cysteine residue of the second polypeptide moiety. The first polypeptide moiety may be a Ub$_{1-75}$ moiety, for example. The second polypeptide moiety may bear a reporter tag, such as a reporter tag selected from the group consisting of affinity tags (e.g., HA-tag, His-tag, FLAG-tag, or Myc-tag), biotin and fluorophores.

Additionally provided by the present invention is a method of making a di- or polyprotein, comprising linking a first polypeptide molecule and a second polypeptide molecule using 3-(2-(bromomethyl)-1,3-dioxolan-2-yl)prop-2-en-1-amine. The first polypeptide molecule may be Ub$_{1-75}$, for instance. The second polypeptide molecule may contain a cysteine residue. For example, the second polypeptide molecule may be a ubiquitin having a cysteine residue at position 6, 11, 27, 29, 33, 48 or 63.

A still further aspect of the invention furnishes a method of making a di- or polyprotein, comprising the steps of:

reacting PP1-C(=O)—S—R$^1$, wherein PP1 is a first polypeptide and —C(=O)—S—R$^1$ is a thioester group (e.g., —S—R$^1$ can be MESNA, i.e., a sodium 2-mercaptoethane sulfonate group, —S(CH$_2$)$_2$SO$_3$Na) with a compound having a structure in accordance with Formula (I):

wherein R is —CH$_2$CH$_2$— or —CH=CH—, Diox is —O(CH$_2$)$_n$O— with n=2 or 3 and forms a 1,3-dioxolane ring or 1,3-dioxane ring which includes the carbon atom to which the oxygen atoms of —O(CH$_2$)$_n$O— are both bonded, and X is Br, Cl or I, to provide PP1-C(=O)NHCH$_2$—R—C(Diox)CH$_2$X;

converting the 1,3-dioxolane ring or the 1,3-dioxane ring to a ketone to provide PP1-C(=O)NH—CH$_2$—R—C(=O)CH$_2$X; and reacting the PP1-C(=O)NH—CH$_2$—R—C(=O)CH$_2$X with a second polypeptide bearing a cysteine residue.

In one embodiment of such a method, the second polypeptide may be a ubiquitin and the cysteine residue may be present at the 6, 11, 27, 29, 33, 48 or 63 position of the ubiquitin. The second polypeptide may bear a reporter tag, such as an affinity tag (HA-tag, His-tag, FLAG-tag, or Myc-tag), biotin or fluorophore. The first polypeptide may be a ubiquitin, such as Ub$_{1-75}$.

DETAILED DESCRIPTION OF CERTAIN EMBODIMENTS OF THE INVENTION

Figure 1:
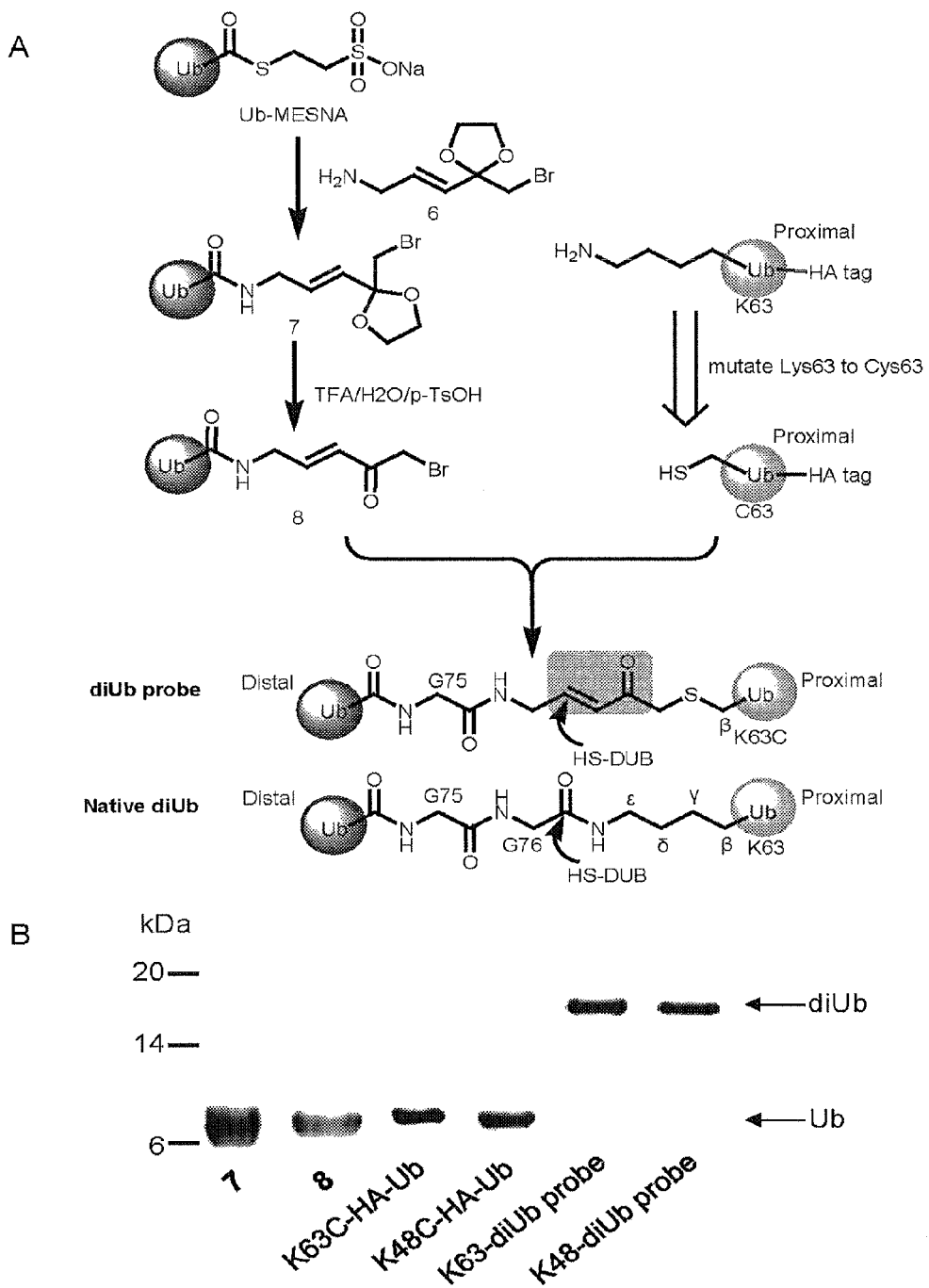
FIG. 1A shows in schematic form the assembly of a diubiquitin in accordance with the present invention, wherein 3-(2-bromomethyl)-1,3-dioxolan-2-yl)prop-2-en-1-amine is used as a linker compound to link together two ubiquitin molecules (Ub), with one of the two ubiquitin molecules bearing a reporter tag (HA-tag).
FIG. 1B illustrates denaturing SDS-gel showing the formation of K63C- and K48C-diUb probes, as further described in the Examples.

The present invention provides a new class of activity-based diubiquitin probes with defined linkages, as illustrated, for example, in FIG. 1. Structurally, they closely mimic the native diubiquitin in the size of the linker. A Michael acceptor may be introduced in the linker (linkage) between the proximal and distal ubiquitin moieties in order to trap the catalytic cysteine thiol of the DUB active site. In order to introduce the Michael acceptor to a diubiquitin (diUb) probe, linker compounds such as 3-(2-bromomethyl)-1,3-dioxolan-2-yl)prop-2-en-1-amine may be utilized. In this embodiment, the linker compound has a structure in accordance with Formula (I):

wherein R is —CH=CH—, Diox is —O(CH$_2$)$_n$O— with n=2 or 3 and forms a 1,3-dioxolane ring or 1,3-dioxane ring which includes the carbon atom to which the oxygen atoms of —O(CH$_2$)O— are both bonded, and X is Br, Cl or I. Such linker compounds harbor a Michael acceptor and act as linkers to conjugate two ubiquitin or other polypeptide moieties. To avoid the ready formation of a Schiff base if an amino group and a carbonyl (ketone) group were to coexist in such a molecule, the carbonyl group is protected in the linker compound by forming a ketal. In another embodiment, the linker compound lacks a carbon-carbon double bond and corresponds to a structure in accordance with Formula (I):

$$H_2NCH_2—R—C(Diox)CH_2X \qquad (I)$$

wherein R is —CH$_2$CH$_2$—, Diox is —O(CH$_2$)$_n$O— with n=2 or 3 and forms a 1,3-dioxolane ring or 1,3-dioxane ring which includes the carbon atom to which the oxygen atoms of —O(CH$_2$)$_n$O— are both bonded, and X is Br, Cl or I. Illustrative examples of linker compounds in accordance with the present invention include, without limitation, the compounds where R, Diox and X are as stated: a) R=—CH$_2$CH$_2$—, Diox=—O—CH$_2$CH$_2$—O—, X=Br; b) R=—CH=CH—, Diox=—O—CH$_2$CH$_2$—O—, X=Br; c) R=—CH$_2$CH$_2$—, Diox=—O—CH$_2$CH$_2$CH$_2$—O—, X=Br; d) R=—CH=CH—, Diox=—O—CH$_2$CH$_2$CH$_2$—O—, X=Br; e) R=—CH$_2$CH$_2$—, Diox=—O—CH$_2$CH$_2$—O—, X=Cl; f) R=—CH=CH—, Diox=—O—CH$_2$CH$_2$—O—, X=Cl; g) R=—CH$_2$CH$_2$—, Diox=—O—CH$_2$CH$_2$CH$_2$—O—, X=Cl; h) R=—CH=CH—, Diox=—O—CH$_2$CH$_2$CH$_2$—O—, X=Cl; i) R=—CH$_2$CH$_2$—, Diox=—O—CH$_2$CH$_2$—O—, X=I; j) R=—CH=CH—, Diox=—O—CH$_2$CH$_2$—O—, X=I; k) R=—CH$_2$CH$_2$—, Diox=—O—CH$_2$CH$_2$CH$_2$—O—, X=I; and l) R=—CH=CH—, Diox=—O—CH$_2$CH$_2$—O—, X=I.

The above-mentioned linker compounds may be used in a similar manner to link together polypeptides other than diubiquitin.

Figure 2:
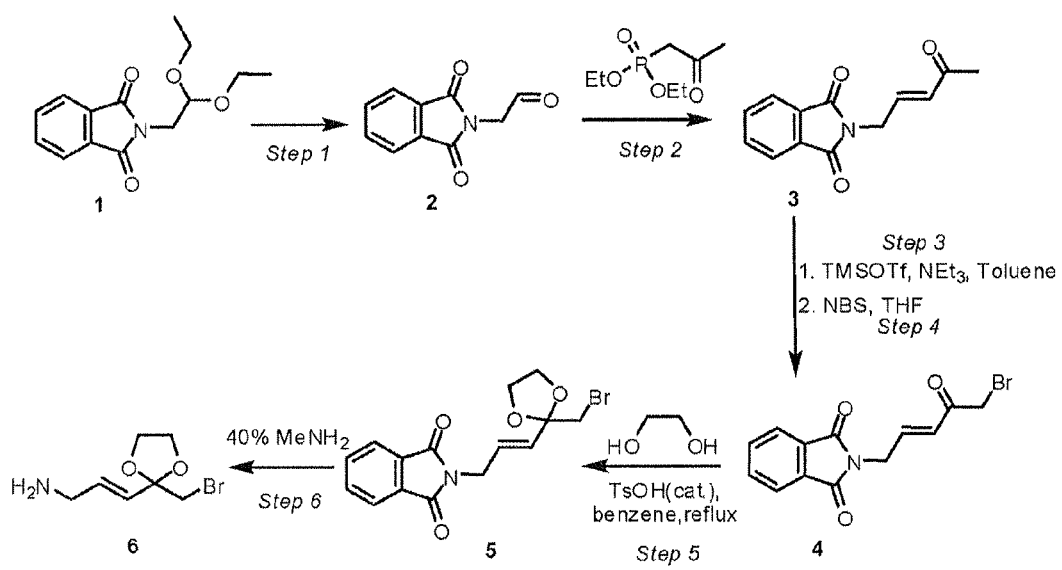
FIG. 2 shows in schematic form a synthetic route for the preparation of the linker compound 3-(2-bromomethyl)-1,3-dioxolan-2-yl)prop-2-en-1-amine.

Synthesis of the Linker Compound 3-(2-Bromomethyl)-1,3-dioxolan-2-yl)prop-2-en-1-amine The compound 3-(2-bromomethyl)-1,3-dioxolan-2-yl)prop-2-en-1-amine which is useful as a linker molecule in accordance with various aspects of the present invention may be synthesized using the route schematically illustrated in FIG. 2. Compound 2 (2-(1,3-dioxoisoindolin-2-yl)acetaldehyde) may be prepared from Compound 1 (phthalimidoacetaldehydediethylacetal) by contacting Compound 1 with trifluoroacetic acid (TFA), whereby the diethylacetal group is converted to an aldehyde group. Compound 2 may then be converted to Compound 3 (2-(4-oxopent-2-enyl)idoindoline-1,3-dione) by reacting Compound 2 with diethyl(2-oxopropyl)phosphonate in the presence of NaH (sodium hydride). This step introduces a Michael acceptor group —CH=CH—C(=O)CH$_3$ into the molecule. Compound 3 may then be converted into Compound 4 (2-(5-bromo-4-oxopent-2-enyl)isoindoline-1,3-dione) by reacting Compound 3 with trimethylsilyl triflate (TMSOTf) in the presence of a tertiary amine such as triethyl amine, to yield an intermediate silyl enol ether. Reaction of the silyl enol ether with NBS (n-bromosuccimide) in the presence of a base such as NaHCO$_3$ yields Compound 4. Other halogenation methods known in the art may be utilized for the purpose of introducing Br, Cl or I on the terminal methyl group that is alpha to the carbonyl functionality. In the next step, Compound 4 is reacted with ethylene glycol in the presence of an acid such as p-toluenesulfonic acid to produce Compound 5 (2-(3-(2-(bromomethyl)-1,3-dioxolan-2-yl)allyl)isoindoline-1,3-dione), which contains a 1,3-dioxolane ring (i.e., a ketal) as a carbonyl protecting group. Alternatively, the carbonyl group may be protected by means of a 1,3-dioxane ring, which may be formed in an analogous way using 1,3-propanediol rather than ethylene glycol. The phthalimido group in Compound 5 may then be converted to a primary amine group through hydrolysis, e.g., base-catalyzed hydrolysis. For example, Compound 5 may be reacted with aqueous methylamine in methanol at approximately room temperature (e.g., about 15° C. to about 35° C.), thereby yielding Compound 6 (3-(2-(bromomethyl)-1,3-dioxolan-2-yl)prop-2-en-1-amine).

Figure 3:
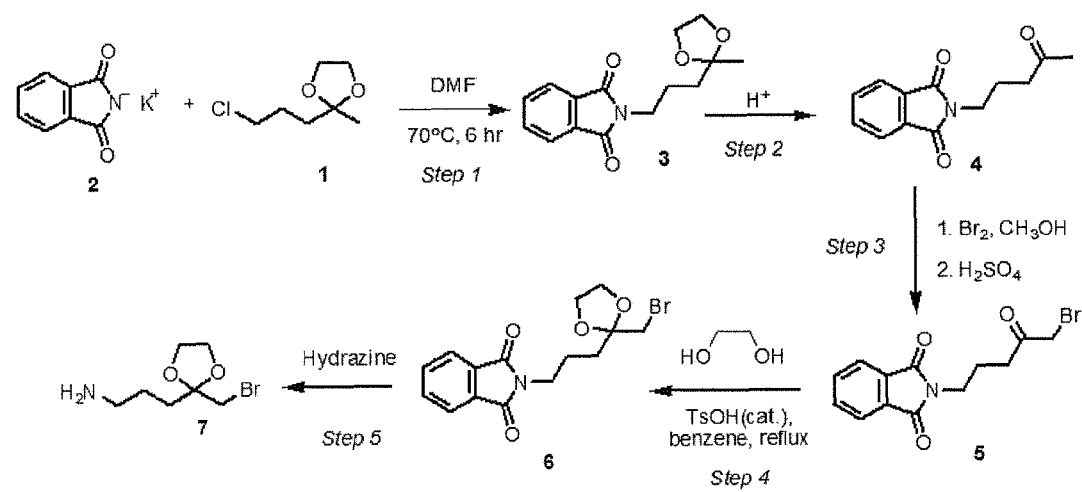
FIG. 3 shows in schematic form a synthetic route for the preparation of the linker compound 3-(2-bromomethyl)-1,3-dioxolan-2-yl)propan-1-amine.

Synthesis of the Linker Compound 3-(2-(Bromomethyl)-1,3-dioxolan-2-yl)propan-1-amine The linker molecule 3-(2-(bromomethyl)-1,3-dioxolan-2-yl)propan-1-amine may be synthesized using the route schematically illustrated in FIG. 3. Compound 3 (2-(3-(2-methyl-1,3-dioxolan-2-yl)propyl)isoindoline-1,3-dione) may be prepared by reacting Compound 1 (phthalimide potassium salt) and Compound 2 (2-(3-chloropropyl)-2-methyl-1,3-dioxolane). Compound 3 may then be converted to Compound 4 (2-(4-oxopentyl)isoindoline-1,3-dione) by treating with TFA. Compound 4 may then be converted into Compound 5 (2-(5-bromo-4-oxopentyl)isoindoline-1,3-dione) by reacting Compound 4 with Br$_2$. In the next step, Compound 5 is reacted with ethylene glycol in the presence of an acid such as p-toluenesulfonic acid to produce Compound 6 (2-(3-(2-(bromomethyl)-1,3-dioxolan-2-yl)propyl) isoindoline-1,3-dione), wherein a 1,3-dioxolane ring has been introduced in order to protect the carbonyl group. Protection of the carbonyl group could alternatively be accomplished by reacting Compound 5 with 1,3-propanediol, thereby introducing a 1,3-dioxane ring. Finally the phthalimido group in Compound 6 may then be converted to a primary amine group through hydrolysis, e.g., base-catalyzed hydrolysis. For example, Compound 6 may be reacted with aqueous hydrazine in methanol at approximately room temperature (e.g., about 15° C. to about 35° C.), thereby yielding Compound 7 (3-(2-(bromomethyl)-1,3-dioxolan-2-yl)propan-1-amine).

Ubiquitin and Other Polypeptide Molecules

The diproteins (e.g., diubiquitins) of the present invention are characterized by having a first polypeptide (e.g., ubiquitin) moiety (residue) and a second polypeptide (e.g., ubiquitin) moiety (residue) which are covalently linked together by the above-mentioned linker compounds (e.g., 3-(2-bromomethyl)-1,3-dioxolan-2-yl)prop-2-en-1-amine or 3-(2-bromomethyl)-1,3-dioxolan-2-yl)propan-1-amine).

Upon reaction with precursors to the first and second polypeptide moieties, as will be described in more detail subsequently, the linker compound becomes incorporated into a linkage having a structure corresponding to —[C(=O) NHCH$_2$C(=O)NH—R—C(=O)CH$_2$SCH$_2$]—. As previously explained, R can be either a saturated —CH$_2$CH$_2$— moiety or an unsaturated —CH=CH— moiety. Thus, the reacted linker compound, where R=—CH=CH—, provides a Michael acceptor-containing moiety —NHCH$_2$CH=CHC(=O)CH$_2$— within the linkage. The moiety —C(=O)NHC(=O)— in the linkage structure may be derived from a glycine residue of a polypeptide, while the moiety —SCH$_2$— may be derived from a cysteine residue of another polypeptide.

The term "polypeptide" as used herein defines an organic compound made up of two or more amino acid residues arranged in a linear chain, wherein the individual amino acids in the organic compound are linked by peptide bonds, i.e., an amide bond formed between adjacent amino acid residues. A polypeptide is sometimes alternatively referred to as a "protein," "peptide," or "peptide sequence." In certain aspects of the present invention, one or both of the first polypeptide moiety and the second polypeptide moiety is a ubiquitin moiety (i.e., a moiety derived from a ubiquitin molecule). Ubiquitin (Ub) is a 76 amino acid small protein. The amino acid sequence of mature human ubiquitin is well known and is set forth, for example, in U.S. Pat. Pub. No. 2014/0072992, the entire disclosure of which is incorporated herein by reference for all purposes.

As will be explained in more detail below, the phrases "ubiquitin molecule" and "ubiquitin" are used herein to refer not only to full-length ubiquitin, but also truncated and/or modified ubiquitins as well as ubiquitin fragments. Incorporation of such a molecule into the diproteins of the present invention provides a ubiquitin moiety in the diprotein (i.e., a residue derived from the ubiquitin molecule). The Ub fragments may be active as substrates and may, in various embodiments of the invention, comprise at least 25%, 30%, 40%, 50%, 60%, 70%, 75%, 80%, 85%, 90%, 95%, 97%, 99% or more of the full-length Ub. The fragment may comprise the C-terminus of ubiquitin.

In one embodiment of the invention, the first ubiquitin moiety is $Ub_{1-75}$ or a fragment thereof, in particular a fragment of $Ub_{1-75}$ (a polypeptide containing residues 1 through 75 of ubiquitin) that comprises at least residues 66 to 75 of $Ub_{1-75}$, i.e., a polypeptide that consists of at least residues 66 to 75 of $Ub_{1-75}$. The C-terminal amino acid residue of $Ub_{1-75}$ or the fragment thereof, which comprises at least residues 66 to 75 of $Ub_{1-75}$, i.e., residue 75 of Ub, may be covalently connected to the linker compound, as described in more detail hereafter.

In a further embodiment of the invention, the second ubiquitin moiety is a ubiquitin moiety containing at least one cysteine residue. Such cysteine residues may be introduced into a ubiquitin molecule by conversion of a lysine residue into a cysteine residue using a mutase technique, for example. In particular aspects of the invention, the second ubiquitin moiety (and thus the ubiquitin molecule from which it is derived) may contain a cysteine residue at position 6, 11, 27, 29, 33, 48 or 63. Mature human ubiquitin has a lysine residue at each of those positions, any one of which may be converted into a cysteine residue reactive with the halomethyl group on the linker compound.

One or both of the polypeptides or polypeptide moieties utilized in the present invention may contain one or more reporter tags. The term "tag" or "reporter tag" as used herein denotes a biochemical marker or label, i.e. an easily recognizable chemical moiety, e.g., a protein, peptide, or small molecule, that is covalently attached to the N-, or C-terminus, preferably the N-terminus of a protein, polypeptide or peptide sequence. Numerous such polypeptide (protein) labels exist and are known and commonly employed by those skilled in the art. Examples of suitable types of reporter tags include affinity labels, e.g., affinity tags (Kimple and Sondek, BioTechniques (2002), 33:578-590), fluorophores, biotin, or radioactive labels. Illustrative reporter tags include an HA-tag (i.e., a tag derived from hemaglutinin), a His-tag (i.e., a polyhistidine tag), a FLAG-tag (N-DYKDDDDK-C), an Myc-tag (N-EQKLISEEDL-C), biotin, and a fluorophore.

Synthesis of Diubiquitins and Other Diproteins in Accordance with Aspects of the Invention In one aspect of the invention, a first polypeptide (e.g., a first ubiquitin molecule) is provided which contains a functional group capable of reacting with the primary amine group of the linker compound (e.g., 3-(2-bromomethyl)-1,3-dioxolan-2-yl)prop-2-en-1-amine) so as to form a covalent bond between the first polypeptide and the linker compound. This general reaction may be schematically represented as:

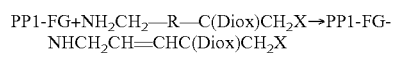

X is Cl, Br or I, PP1 is the first polypeptide, FG is the aforementioned functional group on the first polypeptide, and Diox is —O(CH$_2$)$_n$O— and forms a 1,3-dioxolane ring (when n=2) or a 1,3-dioxane ring (when n=3) which includes the carbon atom to which both of the oxygen atoms of —O(CH$_2$)$_n$O— are bonded. The 1,3-dioxolane ring or 1,3-dioxane ring may thereafter be converted to a carbonyl (—C(=O)—) group by any suitable method, such as treatment with aqueous acid (e.g., p-toluenesulfonic acid dissolved in water and TFA). The reaction product PP1-FG-NHCH$_2$—R—C(=O)CH$_2$X thereby obtained may be referred to as a α-halo-vinylketone-functionalized polypeptide species in the embodiment where R=—CH=CH—.

Groups suitable for use as the functional group FG include thioester groups having the general structure —C(=O)—S—R$^1$. R$^1$ is not particularly limited as long as it does not inhibit or interfere with the desired reaction between the primary amine group of the linker compound with the first polypeptide, wherein —S—R$^1$ is in effect replaced by —NH-L, with L being the remainder of the linker compound other than the primary amine group (for example, —CH$_2$—R—C(Diox)CH$_2$X). R$^1$ may, for example, be a group selected from substituted or unsubstituted aryl groups, substituted or unsubstituted aralkyl groups (e.g., benzyl), and substituted or unsubstituted alkyl groups. Illustrative examples of suitable —S—R$^1$ groups include, but are not limited to, groups derived from benzylmercaptan (—S—CH$_2$-Phenyl), thiophenol (—S-Phenyl), 4-(carboxylmethyl)thiophenol (—S-Phenyl-CH$_2$CO$_2$H), 2-mercaptoethane sulfonic acid and salts thereof (—S—(CH$_2$)$_2$—SO$_3$A, wherein A is H, an alkali metal or ammonium), and 4-mercaptophenyl acetic acid (MPAA) and salts thereof.

For example, the first polypeptide may be a ubiquitin such as $Ub_{1-75}$ which is functionalized at the C-terminus with a sodium 2-mercaptoethane sulfonate (MESNA) group. The MESNA group may be buffered exchanged, for example with HEPES buffer, prior to being reacted with the linker compound. This overall reaction sequence may be represented as follows:

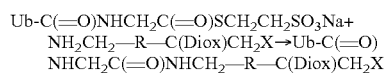

Deprotection of the dioxolane group provides Ub-C(=O) NHCH$_2$C(=O)NHCH$_2$—R—C(=O)CH$_2$X (an α-bromovinylketone-functionalized ubiquitin species, when X=Br and R=—CH=CH—).

In a further aspect of the invention, a second polypeptide (e.g., a second ubiquitin molecule, which may bear at least one reporter tag) is provided which contains a functional group capable of reacting with the halomethyl (e.g., —CH$_2$Cl, —CH$_2$Br, —CH$_2$I) group which is present on the functionalized polypeptide species. For example, the functional group present on the second polypeptide may be a thiol (HS—) group, such as a thiol group provided by a cysteine residue on the second polypeptide. The thiol group displaces the Br, Cl or I in the halomethyl group, thus covalently linking the first polypeptide to the second polypeptide through the formation of a thioether group (e.g., —CH$_2$SCH$_2$—).

This general reaction may be schematically represented as:

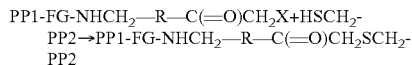

R, X, PP1 and FG have the same meanings as previously and PP2 is the second polypeptide. A diprotein is obtained in which a first polypeptide moiety (PP1) is linked to a second polypeptide moiety (PP2) through a linkage having the structure —[FG-NHCH$_2$—R—C(=O)CH$_2$SCH$_2$]—.

The second polypeptide used in such a reaction may be, for example, a ubiquitin molecule in which the lysine residue at position 6, 11, 27, 29, 33, 48 or 63 has been converted to a cysteine residue. In this case, the linking reaction may be schematically illustrated as follows:

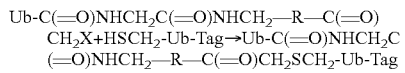

Tag in this case represents a reporter tag, such as an HA tag, which is present on the second ubiquitin molecule. Thus, a diprotein is obtained in which a first (proximal) ubiquitin moiety(Ub-) is linked to a second (distal) uniquitin moiety (-Ub-Tag) through a linkage having the structure —[C(=O)NHCH$_2$C(=O)NHCH$_2$—R—C(=O) CH$_2$SCH$_2$]—. When R is —CH=CH—, the linkage contains a Michael acceptor which is suitable for trapping a DUB active-site cysteine and is of the same approximate size as the linkage found in native diubiquitin.

Uses of Diubiquitins and Other Diproteins in Accordance with Aspects of the Invention In the embodiment where the linkage between ubiquitin molecules contains a moiety having the structure —CH=CH—C(=O)—, the diubiquitins of the invention allow identification and characterization of new DUBs/ULPs (deubiquitinating enzymes/ubiquitin-like-specific proteases) or the identification and characterization of previously unknown substrate specificities/mode of action of known DUBs/ULPs. The main characteristic of such diubiquitins that enables this selectivity is the fact that they are true substrate mimetics. That is, contrary to hitherto known ABPs (activity-based probes), the diubiquitins according to one aspect of the invention contain an ubiquitin which is C-terminally linked via a reactive linkage to another ubiquitin. The linkage contains a Michael acceptor-reactive group that enables covalent capture of the DUB. Accordingly, the diubiquitins in accordance with this embodiment of the invention do not only enable selective capture of DUBs but also allow elucidation of their distinct mechanism of action and their target specificity.

The present invention further provides a method for isolating a deubiquitinating enzyme (DUB) from a sample containing cells or a cell extract, wherein the method comprises the steps of:
(a) treating the sample with a diubiquitin according to the invention; and
(b) separating DUBs.

The separation of DUBs according to step (b) of the method for isolating a DUB may be carried out, for example, using magnetic separation, immunological separation, gel filtration chromatography, affinity chromatography, column chromatography, displacement chromatography, electro chromatography, gas chromatography, high performance liquid chromatography, ion chromatography, micellar electrokinetic chromatography, normal phase chromatography, paper chromatography, reversed-phase chromatography, size exclusion chromatography, thin layer chromatography, gel electrophoresis, centrifugation, adhesion, or flow cytometry.

The diubiquitins according to the present invention can be used as research tools, e.g., as molecular probes to investigate DUBs and the regulation of the ubiquitin system in infection processes and furthermore serve as drug lead structure for novel therapeutics.

The diubiquitins according to the invention can be used to identify ubiquitination sites of target proteins or to detect, purify and/or identify deubiquitinating enzymes (DUBs) with a specificity for a certain target protein or poly-Ub linkage.

The present invention also provides a method for deubiquitinating enzyme analysis of a DUB or a DUB-diubiquitin-protein complex isolated from a sample containing cells or a cell extract using a diubiquitin according to the invention, the method comprising the steps of:
(a) tryptic digestion of the isolated DUB or DUB-diubiquitin-protein complex; and
(b) analysing the product of the tryptic digestion of step (a) by liquid chromatography coupled to mass spectrometry (LC/MS).

The therapeutic use of diubiquitins and other di- and polyproteins according to the present invention as medicaments, or of their pharmacologically acceptable salts, prodrugs, solvates and hydrates and also formulations and pharmaceutical compositions containing the same are within the scope of the present invention. The present invention also relates to the use of these compounds as active ingredient(s) in the preparation or manufacture of a medicament, especially, the use of a diubiquitin of the invention, its pharmacologically acceptable salts, prodrugs or solvates and hydrates and also formulations and pharmaceutical compositions for the treatment of cancer, neurodegenerative disorders, inflammatory diseases, cystic fibrosis, and viral or bacterial infections.

EXAMPLES

Materials and Methods:

1. General Information

Chemical reagents were obtained from Sigma-Aldrich, Alfa and Acros of the highest available grade and used without further purification. $^1$H and $^{13}$C NMR spectra were recorded on Bruker AV400 NMR Spectrometer with a CryoProbe. Chemical shifts are reported in δ (ppm) units using $^{13}$C and residual $^1$H signals from deuterated solvents as references. Mass spectra were recorded on a Shimadzu LCMS 2020 or Waters QTof MS instrument equipped with an electrospray ionization (ESI) source. Analytical thin layer chromatography (TLC) was performed on silica gel 60 GF254 (Merck). Column chromatography was conducted on silica gel (230-400 mesh). Most commercially supplied chemicals were used without further purification. UCH-L1 and OTUB1 were purchased from Boston Biochem.

2. Synthesis of 3-(2-(bromomethyl)-1,3-dioxolan-2-yl)prop-2-en-1-amine (Compound 6 of FIG. 2)

2.1. 2-(1,3-dioxoisoindolin-2-yl)acetaldehyde (Compound 2 of FIG. 2)

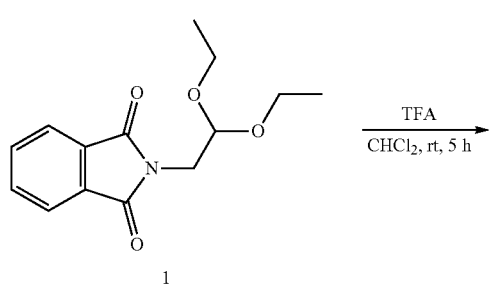

Compound 2 was prepared according to a modified method of Veale et al. (E. B. Veale, J. E. O'Brien, T. McCabe and T. Gunnlaugsson, *Tetrahedron*, 2008, 64, 6794-6800). In an ice/water bath, under a nitrogen atmosphere, to a solution of phthalimido-acetaldehydediethylacetal (13 g, 49 mmol) in CHCl$_3$ (150 mL), TFA (100 mL) was added. The resulting solution was stirred for 1 h. Then the ice bath was removed and the reaction mixture was stirred at r.t. for a further 5 h. The solvent was removed in vacuo and co-evaporated with CH$_2$Cl$_2$ several times to remove the remaining traces of TFA. This yielded the product (Compound 2) as an off-white solid (9 g, 93%). No purification was necessary. $^1$H NMR (CDCl$_3$, 400 MHz) δ 9.68 (s, 1H, CHO), 7.91 (m, 2H), 7.78 (m, 2H), 4.59 (s, 2H); $^{13}$C NMR (CDCl$_3$, 100 MHz): δ (100 MHz, CDCl$_3$) 193.6, 167.6, 134.4, 131.9, 123.7, 47.4.

2.2. 2-(4-oxopent-2-enyl)isoindoline-1,3-dione (Compound 3 of FIG. 2)

Under a nitrogen atmosphere, to a mixture of NaH (560 mg, 22 mmol) and anhydrous THF (90 mL), a solution of diethyle(2-oxopropyl)phosphonate (4.27 g, 22 mmol) in THF (60 mL) was added over 10 min. The resulting solution was stirred at r.t. for 1 h. Then Compound 2 (6.24 g, 33 mmol) was dissolved in THF (30 mL) and was added dropwise to the above solution. The reaction mixture was stirred at r.t. for a further 3 h. The reaction was quenched with H$_2$O, and THF was removed in vacuo. The residue was then extracted with CH$_2$Cl$_2$ and the combined organic layer was washed with $^1$N HCl and saturated NaHCO$_3$, dried over Na$_2$SO$_4$. The solvent was evaporated and the residue was purified by silica gel column chromatography with Hexane/EtOAc (1:1) to provide Compound 3 (4.6 g, 20 mmol, 60%) as a white solid. $^1$H NMR (CDCl$_3$, 400 MHz) δ 7.91 (m, 2H), 7.79 (m, 2H), 6.81-6.74 (m, 1H), 6.16-6.11(dt, J=1.6, 16.0 Hz, 1H), 4.49 (dd, J=1.6, 4.8 Hz, 2H), 2.27 (s, 3H); $^{13}$C NMR (CDCl$_3$, 100 MHz): δ 197.7, 167.7, 139.7, 134.4, 131.9, 131.8, 123.7, 123.6, 38.3, 27.2; MS (ESI, positive) m/z calcd. for C13H12NO3 [M+H]$^+$: 230, found: 230.

2.3. 2-(5-bromo-4-oxopent-2-enyl)isoindoline-1,3-dione (Compound 4 of FIG. 2)

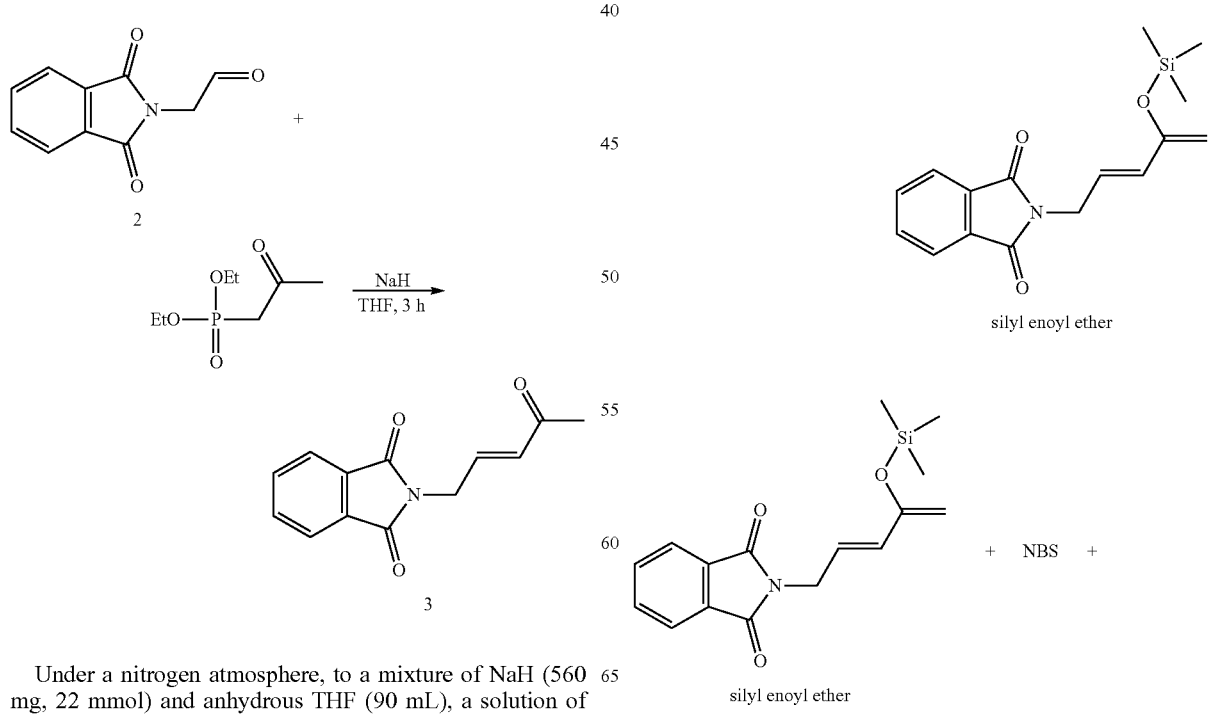

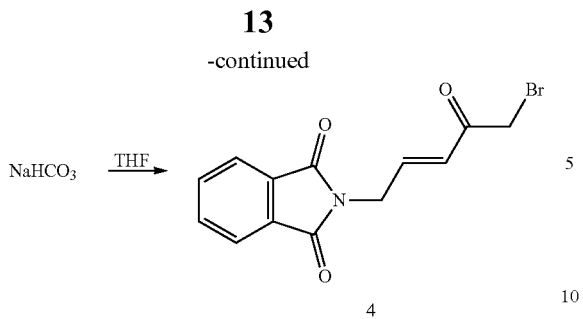
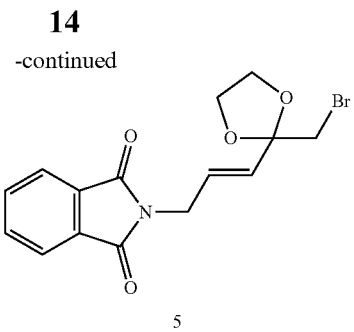

Compound 4 was prepared according to a modified method of Little et al. (T. L. Little and S. E. Webber, *The Journal of Organic Chemistry*, 1994, 59, 7299-7305). Under $N_2$ atmosphere, to 2.18 g (9.56 mmol) of Compound 3 was added 45 mL of toluene containing 2 mL (14.3 mmol) of $NEt_3$. Trimethylsilyl triflate 2.25 mL (12.4 mmol) was dissolved in toluene (10 mL) and was added dropwise to the above solution. The reaction mixture was stirred at r.t. for 16 h, and quenched with 100 mL of saturated aqueous $NaHCO_3$. This mixture was extracted with ether (150 mL) three times. The combined organic layer was washed with $H_2O$, dried with $Na_2SO_4$, and evaporated. The yellow residual oil was directly used for the next step. In an ice/water bath, the silyl enol ether was dissolved in 100 mL of anhydrous THF, and 1.2 g (14.3 mmol) $NaHCO_3$ was added. To the mixture was added NBS 1.9 g (10.5 mmol) and the reaction mixture was stirred for 4 h. Then the ice/water was removed and the reaction was quenched with 50 mL of saturated aqueous $NaHCO_3$. The mixture was then extracted with ether (150 mL) for three times. The combined organic layer was washed with $H_2O$, dried with $Na_2SO_4$. The solvent was evaporated and the residue was purified by silica gel column chromatography with Hexane/EtOAc (3:1) to provide compound 4 (1.46 g, 4.74 mmol, 50%) as a white solid. $^1H$ NMR ($CDCl_3$, 400 MHz) δ 7.92 (m, 2H), 7.79 (m, 2H), 6.98-6.92 (m, 1H), 6.41-6.36 (dt, J=1.6, 15.6 Hz, 1H), 4.53 (dd, J=1.6, 5.2 Hz, 2H), 4.01 (s, 2H); $^{13}C$ NMR ($CDCl_3$, 100 MHz): δ 190.1, 167.6, 141.7, 134.4, 131.9, 127.3, 123.7, 38.4, 32.7; MS (ESI, positive) m/z calcd. for $C13H11BrNO_3$ $[M+H]^+$: 308, 310, found: 308, 310.

2.4. 2-(3-(2-(bromomethyl)-1,3-dioxolan-2-yl)allyl)isoindoline-1,3-dione (Compound 5 of FIG. 2)

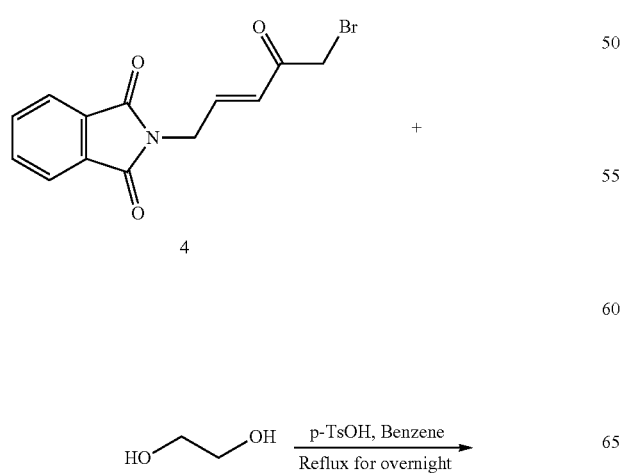

Under $N_2$ atmosphere, to the mixture of Compound 4 (1.46 g, 4.74 mmol) in 250 mL of benzene was added ethylene glycol (2.94 g, 47 mmol) and p-toluenesulfonic acid (90 mg, 0.47 mmol). The reaction mixture was refluxed for overnight, during which $H_2O$ was removed using Dean-Stark trap. After cooling to room temperature, the reaction was quenched with 50 mL of saturated $NaHCO_3$. The mixture was extracted with ether. The combined organic layer was washed with $H_2O$, dried with $Na_2SO_4$. The solvent was evaporated and the residue was purified by silica gel column chromatography with Hexane/EtOAc (4:1) to provide Compound 5 (0.9 g, 2.56 mmol, 54%) as a white solid. $^1H$ NMR ($CDCl_3$, 400 MHz) δ 7.89 (m, 2H), 7.75 (m, 2H), 6.06-6.00 (m, 1H), 5.73-5.68 (dt, J=1.6, 15.6 Hz, 1H), 4.35 (dd, J=1.6, 6.0 Hz, 2H), 4.10-3.93 (m, 4H), 3.47 (s, 2H); $^{13}C$ NMR ($CDCl_3$, 100 MHz): δ 167.8, 134.1, 132.0, 130.1, 127.3, 123.4, 105.6, 65.8, 38.4, 36.4; MS (ESI, positive) m/z calcd. for $C15H15BrNO_4$ $[M+H]^+$: 352, 354, found: 352, 354.

2.5. 3-(2-(bromomethyl)-1,3-dioxolan-2-yl)prop-2-en-1-amine (Compound 6 of FIG. 2)

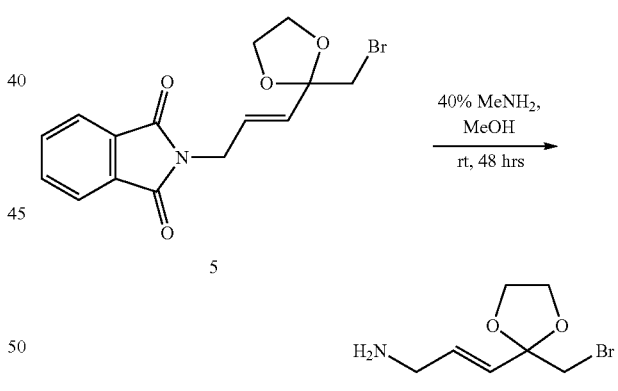

Under $N_2$ atmosphere, to a mixture of Compound 5 (900 mg, 2.56 mmol) and 100 mL of methanol was added 10 mL 40% $MeNH_2$. The reaction mixture was stirred at r.t. for 48 h. The solvent was evaporated and the residue was purified by silica gel column chromatography with $NH_3$ saturated $CH_2Cl_2/CH_3OH$ (20:1) to provide Compound 6 (300 mg, 1.35 mmol, 53%) as a yellow oil. $^1H$ NMR ($CDCl_3$, 400 MHz) δ 6.06-6.00 (m, 1H), 5.57 (d, J=15.2 Hz, 1H), 4.04-3.89 (m, 4H), 3.43 (s, 2H), 3.40-3.34 (m, 2H), 1.84 (bs, 2H); $^{13}C$ NMR ($CDCl_3$, 100 MHz): δ 134.6, 133.9, 126.9, 106.0, 105.8, 65.7, 65.4, 42.6, 36.5; MS (ESI, positive) m/z calcd. for $C7H13BrNO_2$ $[M+H]^+$: 222, 224, found: 222, 224.

3. Expression and Purification of Ubiquitin and DUBs
3.1. Generation of hUb$_{1-75}$-MESNa The hUb$_{1-75}$-pTYB1 plasmid was constructed by cloning the sequence of human Ub (lacking Gly76) into the pTYB1 vector (New England Biolabs). The resulting plasmid was confirmed by DNA sequencing. For protein expression, the plasmid was transformed into BL21(DE3) cells. Cells were cultured at 37° C. in LB medium (10 L) containing 100 μg/ml ampicillin. The cell culture was induced with 0.4 mM IPTG at OD$_{600}$ of 0.6~0.8, and grown for an additional 18 hrs at 15° C. Cells were harvested by centrifugation at 8,000 g for 30 mins and resuspended in lysis buffer (20 mM Tris, 200 mM NaCl, 1 mM EDTA, 5% glycerol, pH 7.5). Cells were lysed by sonication and the resulting lysate was cleared by centrifugation at 38,000 g for 30 mins. The supernatant was incubated with 50 mL chitin resin (New England Biolabs) at 4° C. for 6 hr. The resin was then washed with 500 ml of high salt wash buffer (20 mM Tris, 1 M NaCl, 1 mM EDTA, 5% glycerol, pH 7.5) and 300 ml of low salt wash buffer (50 mM MES, 100 mM NaCl, pH 6.5). The resin was then incubated with 50 ml cleavage buffer (50 mM MES, 100 mM NaCl, 75 mM β-mercaptoethanesulfonic acid sodium salt (MESNa)) for 12 hrs at room temperature. The molecular weight of the Ub-MESNA species was determined by ESI-MS to 8633 Da (theoretical MW is 8632 Da).

3.2. Generation of HA-K63C-hUb$_{1-76}$ and HA-K48C-hUb$_{1-76}$

HA-K63C-hUb$_{1-76}$ and HA-K48C-hUb$_{1-76}$ plasmids were constructed by Quikchange to generate mutant ubiquitin pTYB1 plasmids (New England Biolabs). The resulting plasmid was confirmed by DNA sequencing. For protein expression, the plasmid was transformed into BL21(DE3) cells. Cells were cultured at 37° C. in LB medium (10 L) containing 100 μg/ml ampicillin. The cell culture was induced with 0.4 mM IPTG at OD$_{600}$ of 0.6~0.8, and grown for an additional 18 hrs at 15° C. Cells were harvested by centrifugation at 8,000 g for 30 mins and resuspended in lysis buffer (20 mM Tris, 200 mM NaCl, 1 mM EDTA, 5% glycerol, pH 7.5). Cells were lysed by sonication and the resulting lysate was cleared by centrifugation at 38,000 g for 30 mins. The supernatant was incubated with 50 mL chitin resin (New England Biolabs) at 4° C. for 6 hr. The resin was then washed with 500 ml of high salt wash buffer (20 mM Tris, 1 M NaCl, 1 mM EDTA, 5% glycerol, pH 7.5) and 300 ml of low salt wash buffer (50 mM Tris, 100 mM NaCl, pH 8.5). The resin was then incubated with 50 ml cleavage buffer (50 mM Tris, 100 mM NaCl, 250 mM DTT, pH 7.7) for 12 hrs at room temperature. The molecular weight of the K63C-hUb$_{1-76}$ species was determined by ESI-MS to 9753 Da (theoretical MW is 9752 Da). The molecular weight of the K48C-hUb$_{1-76}$ species was determined by ESI-MS to 9753 Da (theoretical MW is 9752 Da).

3.3. Expression and Purification of USPs

The USP2 and USP7 genes were purchased from Addgene. USP2 (residues 259-605) and USP7 (residues 208-564) were cloned into pET28a following the reported protocols (W. P. Bozza, Q. Liang, P. Gong and Z. Zhuang, *Biochemistry-Us*, 2012, 51, 10075-10086; M. Renatus, S. G. Parrado, A. D'Arcy, U. Eidhoff, B. Gerhartz, U. Hassiepen, B. Pierrat, R. Riedl, D. Vinzenz, S. Worpenberg and M. Kroemer, *Structure*, 2006, 14, 1293-1302; Alex C. Faesen, Annette M. G. Dirac, A. Shanmugham, H. Ovaa, A. Perrakis and Titia K. Sixma, *Molecular Cell*, 2011, 44, 147-159). USP8 (residues 734-1110) was kindly provided by Dr. Sirano Dhe-Phaganon (see G. V. Avvakumov, J. R. Walker, S. Xue, P. J. Finerty, Jr., F. Mackenzie, E. M. Newman and S. Dhe-Paganon, *J Biol Chem*, 2006, 281, 38061-38070). USP21 (residues 209-562) in pET28a-LIC was purchased from Addgene.

4. Synthesis of diUb Probes
4.1. Generation of Ubiquitin Species 7

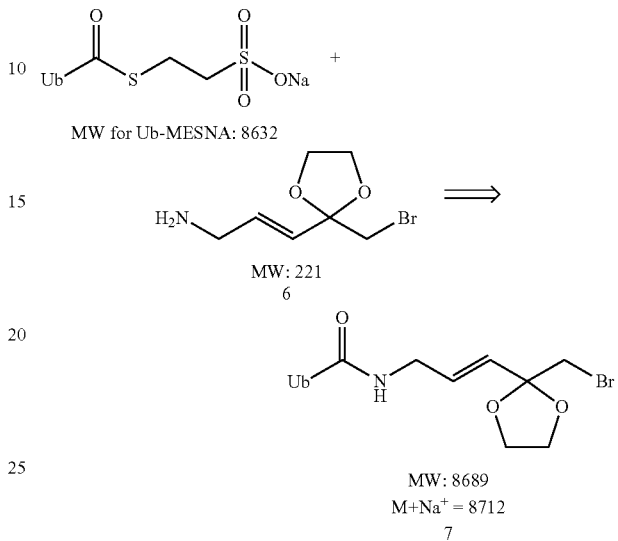

Before the ligation of hUb$_{75}$-MESNA with Compound 6, hUb$_{75}$-MESNA was buffer exchanged with HEPES buffer (pH 6.7). To a solution of hUb$_{75}$-MESNA (3 mg/mL) was added 0.4 M of compound 6 (dissolved in the HEPES buffer). The mixture was immediately vortexed and reacted at r.t. overnight. Then the resulting product was buffer exchanged to remove unreacted Compound 6. The molecular weight of the ubiquitin species 7 was determined by ESI-MS to be 8713 Da (theoretical MW is 8712 Da).

4.2. Generation of Ubiquitin Species 8

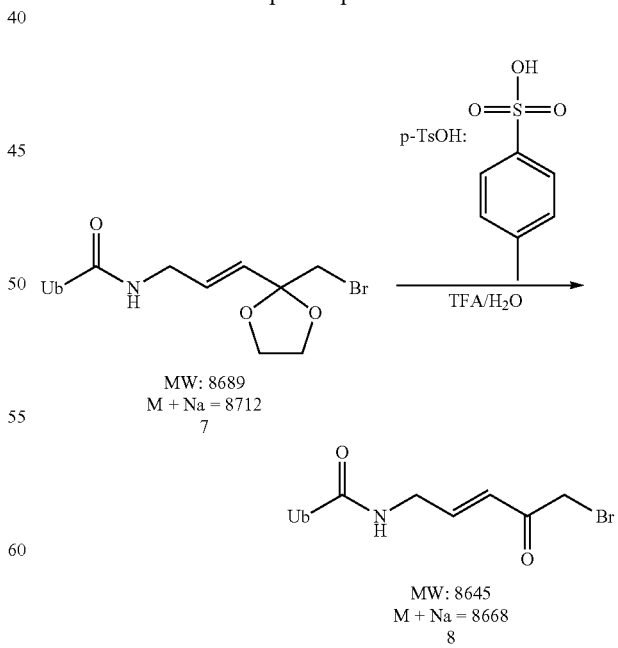

Ubiquitin species 7 was added to a solution of p-TsOH dissolved in H$_2$O and TFA to obtain a solution containing 0.04 M p-TsOH, 54% (v/v) TFA and 0.5 mg/mL ubiquitin species 7. The reaction was allowed to continue at r.t. for 0.5 hr. The crude mixture was precipitated with ten times volume of cold ether, washed with cold ether and air dried. Then the crude product was dissolved in buffer (100 mM $Na_2HPO_4$, 8 M urea; 500 mM NaCl, pH 6.0) at a protein concentration of approximately 0.5 mg/ml and dialyzed against folding buffer (20 mM $Na_2HPO_4$, 100 mM NaCl, pH 6.0). The molecular weight of the ubiquitin species 8 was determined by ESI-MS to be 8669 Da (theoretical MW is 8668 Da).

4.3. Generation of the Diubiquitin (diUb) Probes

In order to form a K63-diUb probe, ubiquitin species 8 was mixed with K63C-HA-Ub at a concentration of 0.5 mg/mL for both ubiquitin species. The mixture was incubated at r.t. overnight. SDS-PAGE gel was used to detect the formation of diUb (FIG. 1B). Then the reaction product was purified by a cation-exchange SP Sepharose HP column (GE Life Sciences) using a FPLC system. The protein solution was first buffer exchanged into buffer A (100 mM ammonium acetate, 100 mM NaCl, pH 4.5) using a Centricon (3 kDa MWCO). The sample was loaded to a preequilibrated SP column and,then eluted at a flow rate of 1 ml/min using a gradient of 0 to 65% buffer B (100 mM ammonium acetate, 1 M NaCl, pH 4.5). Fractions were collected in 1 ml volume, and those containing pure diubiquitin were pooled and concentrated. K48-diUb probe was prepared and purified by the same method as described for K63-diUb probe.

5. DUB Labeling Assays 5.1. Reactivity of diUb Probes Towards Different DUBs

DUBs (1 μg) were incubated with 1 μg different probes at room temperature for 2 hours in a reaction buffer containing 50 mM HEPES (pH 7.0), 100 mM NaCl. Then the reaction was quenched by the addition of the SDS-PAGE 6X loading solution. Samples were resolved by reducing SDS-PAGE gel and then stained with Coomassie brilliant blue for detection. For Western blotting the protein samples were transferred to a PVDF membrane and detected by anti-HA antibody as previously described (J. Chen, Thomas S. Dexheimer, Y. Ai, Q. Liang, Mark A. Villamil, J. Inglese, David J. Maloney, A. Jadhav, A. Simeonov and Z. Zhuang, *Chemistry & Biology*, 2011, 18, 1390-1400).

To evaluate the effect of reducing agents DTT or β-ME on the reactivity of diUb probes with DUBs, 100, 250 mM DTT or 250 mM β-ME was added to DUBs before the addition of probes.

To assess the effect of denaturing conditions on the reaction of diUb probes with DUBs, 1% SDS or 3 M guanidine hydrochloride was added to DUBs before the addition of probes.

5.2. Preparation of HEK293T Cell Extracts and DUB Activity-Based Profiling Assay This assay was done according to a reported protocol (M. Altun, H. B. Kramer, L. I. Willems, J. L. McDermott, C. A. Leach, S. J. Goldenberg, K. G. Kumar, R. Konietzny, R. Fischer, E. Kogan, M. M. Mackeen, J. McGouran, S. V. Khoronenkova, J. L. Parsons, G. L. Dianov, B. Nicholson and B. M. Kessler, *Chemistry & biology*, 2011, 18, 1401-1412). HEK293T cells were seeded in 10 cm plates, incubated at 37° C. for overnight, and then harvested. Cells were incubated on ice for 1 hour, and lysed on ice in lysis buffer containing 50 mM Tris (pH 7.4), 150 mM NaCl, 5 mM $MgCl_2$, 0.5 mM EDTA, 5 mM DTT, 2 mM ATP, 0.5% NP40, and 10% glycerol. 50 μg Cell lysates were then incubated with 0.2 μM HA-hUb-VME, K63-linked HA-diUb probe and K48-linked HA-diUb probe respectively at room temperature for 3 hours in a labeling solution containing 50 mM Tris (pH 7.0), 5 mM $MgCl_2$, 0.5 mM EDTA, 2 mM DTT, 2 mM ATP, and 250 mM sucrose. Samples were separated by SDS-PAGE, transferred onto nitrocellulose membrane and blotted with anti-HA antibody (Sigma). HRP-conjugated anti-mouse (Sigma) was used as the secondary antibody. Signals were detected using ECL Western blotting substrate (Thermo Fisher).

What is claimed is:

1. A compound having a structure in accordance with Formula (I):

wherein R is —$CH_2CH_2$— or —CH=CH—, Diox is —O($CH_2$)$_n$O— with n=2 or 3 and forms a 1,3-dioxolane ring or 1,3-dioxane ring which includes the carbon atom to which the oxygen atoms of —O($CH_2$)$_n$O— are both bonded, and X is Br, Cl or I.

2. The compound of claim 1, wherein R is —CH=CH—, n=2, and X is Br.

3. The compound of claim 1, wherein R is —$CH_2CH_2$—, n=2, and X is Br.

4. A method of making the compound of claim 1, comprising hydrolyzing a precursor compound having a structure in accordance with Formula (II):

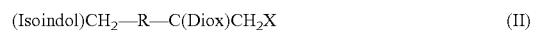

wherein Isoindol is an isoindoline-1,3-dione moiety, R is —$CH_2CH_2$— or —CH=CH—, and Diox is —O($CH_2$)$_n$ O— with n=2 or 3 and forms a 1,3-dioxolane ring or 1,3-dioxane ring which includes the carbon atom to which the oxygen atoms of —O($CH_2$)$_n$ O— are both bonded, and X is Br, Cl or I.

5. The method of claim 4, wherein the precursor compound has been prepared by reacting a compound having a structure in accordance with Formula (III):

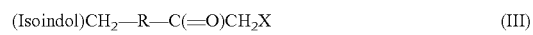

with ethylene glycol or 1,3-propanediol.

6. A method of making a di- or polyprotein, comprising linking a first polypeptide molecule and a second polypeptide molecule using a compound having a structure in accordance with Formula (I):

wherein R is —$CH_2CH_2$— or —CH=CH—, Diox is —O($CH_2$)$_n$O— with n=2 or 3 and forms a 1,3-dioxolane ring or 1,3-dioxane ring which includes the carbon atom to which the oxygen atoms of —O($CH_2$)$_n$O— are both bonded, and X is Br, Cl or I.

7. The method of claim 6, wherein the first polypeptide molecule is $Ub_{1-75}$.

8. The method of claim 6, wherein the second polypeptide molecule contains a cysteine residue.

9. The method of claim 6, wherein the second polypeptide molecule is a ubiquitin having a cysteine residue at position 6, 11, 27, 29, 33, 48 or 63.

10. A method of making a di- or polyprotein, comprising the steps of:
a) reacting PP1-C(=O)—S—$R^1$, wherein PP1 is a first polypeptide and —C(=O)—S—$R^1$ is a thioester group, with a compound having a structure in accordance with Formula (I):

wherein R is —$CH_2CH_2$— or —CH=CH—, Diox is —O($CH_2$)$_n$O— with n=2 or 3 and forms a 1,3-dioxolane ring or 1,3-dioxane ring which includes the carbon atom to which the oxygen atoms of —O(CH$_2$)$_n$O— are both bonded, and X is Br, Cl or I to provide PP1-C(=O)NHCH$_2$—R—C(Diox)CH$_2$X;
b) converting the 1,3-dioxolane ring or 1,3-dioxane ring to a ketone to provide PP1-C(=O)NH—CH$_2$—R—C(=O)CH$_2$X; and
c) reacting the PP1-C(=O)NH—CH$_2$—R—C(=O)CH$_2$X with a second polypeptide bearing a cysteine residue.

11. The method of claim 10, wherein the second polypeptide is a ubiquitin and the cysteine residue is present at the 6, 11, 27, 29, 33, 48 or 63 position of the ubiquitin.

12. The method of claim 10, wherein the second polypeptide bears a reporter tag.

13. The method of claim 12, wherein the reporter tag is selected from the group consisting of affinity tags, biotin and fluorophores.

14. The method of claim 12, wherein the reporter tag is an affinity tag selected from the group consisting of HA-tag, His-tag, FLAG-tag, and Myc-tag.

15. The method of claim 10, wherein the first polypeptide is a ubiquitin.

16. The method of claim 10, wherein the first polypeptide is Ub$_{1-75}$.

17. The method of claim 10, wherein R is —CH$_2$CH$_2$—, n=2, and X is Br.

18. The method of claim 10, wherein R is —CH=CH—, n=2 and X is Br.

* * * * *